United States Patent
Williams

(10) Patent No.: US 8,113,826 B2
(45) Date of Patent: Feb. 14, 2012

(54) BIASED PALATAL BONE EXPANDER

(76) Inventor: Michael O. Williams, Gulfport, MS (US)

( * ) Notice: Subject to any disclaimer, the term of this patent is extended or adjusted under 35 U.S.C. 154(b) by 273 days.

(21) Appl. No.: 12/384,799

(22) Filed: Apr. 9, 2009

(65) Prior Publication Data

US 2010/0261130 A1    Oct. 14, 2010

(51) Int. Cl.
*A61C 3/00* (2006.01)
(52) U.S. Cl. .......................................................... 433/7
(58) Field of Classification Search ............... 433/7, 19, 433/18
See application file for complete search history.

(56) References Cited

U.S. PATENT DOCUMENTS

| | | | |
|---|---|---|---|
| 5,645,422 A | 7/1997 | Williams | |
| 5,769,631 A | 6/1998 | Williams | |
| 6,241,517 B1 | 6/2001 | Williams | |
| 6,328,745 B1 | 12/2001 | Ascherman | |
| 6,358,255 B1 * | 3/2002 | Testa | 606/105 |
| 6,402,510 B1 | 6/2002 | Williams | |
| 6,520,772 B2 | 2/2003 | Williams | |

\* cited by examiner

*Primary Examiner* — Cris L Rodriguez
*Assistant Examiner* — Mirayda A Aponte
(74) *Attorney, Agent, or Firm* — Paul M. Denk

(57) ABSTRACT

A biased palatal bone expander attaches directly to the palatal bone in the roof of the mouth of a patient. The expander has dual, biased, mutually parallel rods. The rods extend from coaxial tubes and have coaxial springs. The expansion of the springs urges the rod outwardly from the center of the expander thus widening the maxillary arch incrementally without a connection upon the teeth. The tubes and rods each attach to two mutually parallel bars perpendicular to the rods. Each bar has two opposite ends with an eyelet upon each end. The eyelets receive screws for securing the expander to a patient. Additionally, the appliance may include a thermoformed shell that a surgeon or orthodontist uses to guide positioning the appliance for installation.

2 Claims, 2 Drawing Sheets

US 8,113,826 B2

BIASED PALATAL BONE EXPANDER

CROSS REFERENCE TO RELATED APPLICATION

This application claims priority to the pending non-provisional application, as a continuation application, upon the application having Ser. No. which application claims priority as a continuation-in-part application upon the application having Ser. No. 11/408,681, filed on Jul. 1, 2006, and now U.S. Pat. No. 7,500,851, and which is commonly owned by the same inventor; and which application claimed priority as a continuation-in-part application upon Ser. No. 10/439,638, filed on May 16, 2003, and now U.S. Pat. No. 7,094,051; which is commonly owned by the same inventor, and which is a continuation-in-part of application Ser. No. 10/186,604, filed Jul. 2, 2002, now U.S. Pat. No. 6,877,982, which is a continuation-in-part of application Ser. No. 09/975,633, filed Oct. 12, 2001, now U.S. Pat. No. 6,719,557, and which is a continuation-in-part of application Ser. No. 09/750,527, filed Dec. 29, 2000, now U.S. Pat. No. 6,520,772, which is a continuation-in-part of application Ser. No. 09/598,766, filed Jun. 22, 2000, now U.S. Pat. No. 6,402,510, which is a continuation-in-part of application Ser. No. 09/406,426, filed Sep. 27, 1999, now U.S. Pat. No. 6,241,517, which is a continuation-in-part of application Ser. No. 09/143,071, filed Aug. 28, 1998, now U.S. Pat. No. 6,036,488, which, in turn, is a continuation-in-part of application Ser. No. 09/065,344, filed Apr. 23, 1998, now U.S. Pat. No. 5,919,042, which is related to application Ser. No. 08/526,686, filed Sep. 11, 1996, now U.S. Pat. No. 5,645,422, and related to Ser. No. 08/688,110, filed Jul. 29, 1996, now U.S. Pat. No. 5,769,631, all of which are incorporated herein by reference.

BACKGROUND OF THE INVENTION

This invention relates generally to orthodontic appliances for expanding the upper, or maxillary, jaw of a person. And more specifically the invention pertains to an expander connected directly to the palate of a person, without using bands or crowns upon teeth, thus adjusting the shape of the maxillary jaw while improving the appearance of a person's mouth and teeth through usage of the present invention.

Over a long time, orthodontists labored towards correcting tooth positions and related jaw conditions to remedy various conditions afflicting patients. Such conditions include overbite and underbite, improper chewing, dental speech impediments, hygiene, and appearance. As a further complication to patients, the lower jaw, or mandible, may grow during a person's lifetime and affect the alignment of teeth in both jaws. To begin, each tooth can be rotated and translated into a new location or orientation as it secures to the jaw with a periodontal ligament. Though extremely strong, the periodontal ligament stretches like other ligaments as a tooth moves. Generally, a tooth is moved in increments from an initial to a final position, often along a standard arc like shape.

Orthodontists use many devices and therapies to move teeth while remedying conditions. Common braces have a wire secured to brackets or bands upon teeth. The brackets were once adhered to the exterior face of a tooth but presently the demands of patients call for securing the brackets to the interior face of a tooth. A wire then is placed upon the bracket and secured by small diameter elastic bands. The arcuate shape of the wire corresponds to the desired position of teeth. Wires have sizes that increase incrementally in diameter and hence rigidity so changing wires from smaller to larger diameters over time generally moves the teeth into a desired position. Each tooth attains its desired position according to the orthodontic treatment plan through the rigidity of the wire. Brackets generally are used in positions rearward from the incisors.

For following an orthodontic plan, an orthodontist may have to create additional space along the jaw to ease tooth movement. Moving teeth rearward opens the space for guiding teeth towards their final positions. An orthodontist applies bands to the molars and if needed, teeth towards the front of the mouth. A band generally adheres to and surrounds a tooth. A fitting generally upon the exterior of a band secures the end of a wire used to establish a desired arc for the teeth on a jaw. Bands also have sockets, generally horizontal, upon the exterior that cooperate with headgear having interior rods received into the sockets upon the molars and an integral outer bow. The outer bow connects to an adjustable strap around the patient's neck. The strap provides a rearward force into the bow and the interior rods to move the molars rearward. This action opens additional space for other teeth that then move to desired positions upon the jaw.

Beyond moving individual teeth along a jaw, an orthodontist may open space for teeth where a jaw has a too narrow shape. A jaw widens while gently pushing the molars outwardly. As above, molars were moved outwards using bands connected to a threaded jack. A coaxial rod connected to a moving bar, or wing for a jack that a threaded cylinder with keyholes for adjusting the length of the rod. A patient performed these adjustments by inserting a key into the keyholes on a prescribed schedule and turning the cylinder a certain amount of rotation. Turning the cylinder urged the wings outwards and the jack against the molars to expand the jaw, most often the maxillary jaw.

Lately, the orthodontic community and manufacturers have developed mouth pieces that fit over teeth while guiding them into new positions. A translucent polymer material forms the mouthpieces as they fit over the teeth, as found initially by the orthodontist, without the bands, wires, and brackets of the prior art. Manufacturers, such as Invisalign® among others, provide mouth pieces, generally modeled in three dimensions by proprietary software for locating teeth in proper positions. The mouth pieces, akin to prior art wires, gently move teeth incrementally over time. The mouth pieces can be worn during the daytime without any perception by people other than a patient. An orthodontist prescribes the mouth pieces in stages which then guide the amount of tooth movement. Friction between the mouth piece and the surface of the teeth generally holds the mouth piece in place. Aligning teeth well along an arc, the mouth pieces do not yet provide expansive lateral forces to widen a jaw or alternatively to contract a jaw.

Attempting to provide expansive lateral forces, the prior art merges a mouthpiece with an expansion device. Vacuuming forming connects an expansion device to a separately manufactured mouthpiece. Further, an expansion device may join to a mouthpiece from pelletized plastic or acrylic placed irregularly upon the surface of a union of the expansion device and a mouthpiece. The junction and the pellets of plastic are then heated or chemically treated to bond the expansion device to the mouthpiece.

DESCRIPTION OF THE PRIOR ART

Others in the prior art have sought to adjust the skeletal foundation of the palate of a person. The Ascherman U.S. Pat. No. 6,328,745, describes a palate expander for application to people of various ages. This expander can guide the movement of four sections of palate following osteomy, or surgical division, of the palatal bone. This expander has a threading system upon two rigid sections and two downwardly extending members upon each section that connect to the palate. The threading system can have one or two rods within matching cylinders attached to the same surface of the rigid sections. The threading system generally extends one but not both of the rigid sections unlike the present invention that advances both. The downwardly extending members terminate in generally planar foot pads unlike the eyelets of the present invention.

Further, the prior U.S. Pat. No. 6,520,772 to Williams shows a bimaxillary appliance for expanding the upper jaw. This appliance has a plate for placement within the teeth of the upper jaw and bands upon its perimeter for connection to the teeth. The plate has an encasement that receives an expansion mechanism. The expansion mechanism has a housing that receives an advancing member in a telescoping manner. The housing member has two parallel spaced apart posts and a centered threaded rod. Springs upon each rod engage the advancing member and bias the advancing member outwardly. The threaded rod directs an activation wing that moves the springs outwardly from the housing in a controlled manner. This patent also describes various Herbst like mechanisms where a rod engages a hollow tube upon bosses. The rods and tubes cooperate to redirect the lower jaw in relation to the upper jaw. Though this patent shows an expansion mechanism using springs, the mechanism lacks direct attachment to the palatal bone structure in a patient.

SUMMARY OF THE INVENTION

The present invention provides a biased palatal bone expander that attaches directly to the palatal bone generally in the roof of the mouth of a patient. The expander has dual, biased, mutually parallel rods. The rods extend from coaxial tubes and within coaxial springs. The expansion of the springs pushes the rod outwardly from the center of the expander thus widening the maxillary arch incrementally without brackets or bands upon the teeth. The tubes attach to a bar perpendicular to the rods and the rods also attach to another bar mutually parallel to the bar beneath the tubes. Each bar has two opposite ends with an eyelet upon each end. The eyelets receive screws for securement of the appliance to a patient. Additionally, the appliance may include a thermoformed shell that aids a surgeon or orthodontist in positioning the appliance for installation.

Numerous objects, features and advantages of the present invention will be readily apparent to those of ordinary skill in the art upon a reading of the following detailed description of presently preferred, but nonetheless illustrative, embodiments of the present invention when taken in conjunction with the accompanying drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and devices for carrying out the several purposes of the present invention. It is important, therefore, that the claims be regarded as including such equivalent constructions insofar as they do not depart from the spirit and the scope of the present invention.

It is, therefore, the principal object of this invention to provide a biased palatal bone expander for adjusting the maxillary arch in a patient without permanently attaching to a patient's teeth.

Another object of the invention provides for a biased palatal bone expander that provides laterally expanding forces while deterring the lengthening of the maxillary arch.

Yet another object of the invention provides for a biased palatal bone expander that includes symmetric expansion apparatus operatively connected to the maxillary arch.

Yet another object of the invention provides for a biased palatal bone expander that includes an expansion apparatus operatively connected to the palatal bone by mechanical fasteners.

Yet another object of the invention provides for a biased palatal bone expander that includes a shell upon the teeth of the maxillary jaw that positions the appliance for installation.

These and other objects may become more apparent to those skilled in the art upon review of the summary of the invention as provided herein, and upon undertaking a study of the description of its preferred embodiment, in view of the drawings.

BRIEF DESCRIPTION OF THE DRAWINGS

In referring to the drawings.

The same reference numerals refer to the same parts throughout the various figures.

DESCRIPTION OF THE PREFERRED EMBODIMENT

Figure 1:
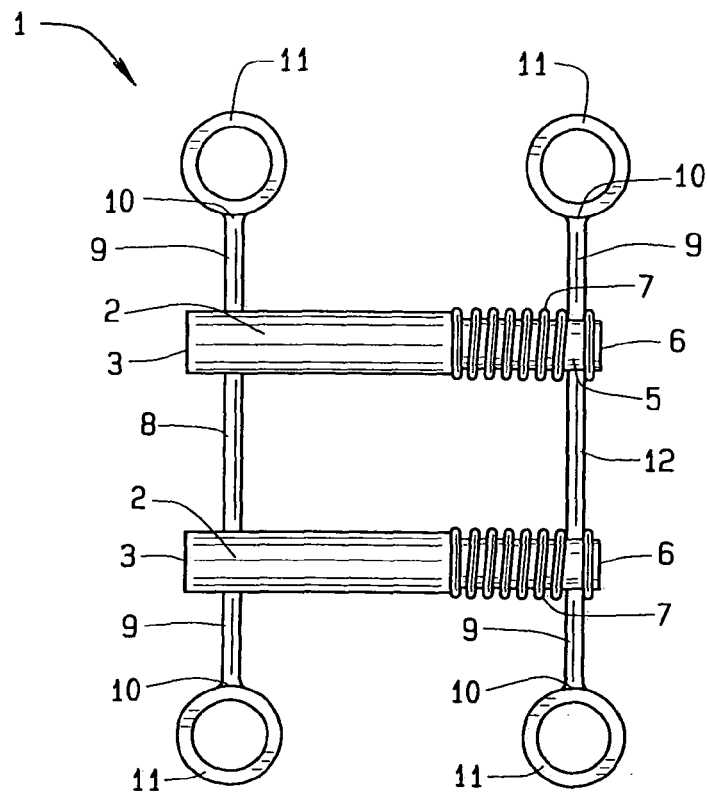
FIG. 1 shows a top view of the present invention.

In referring to the drawings, FIG. 1 shows the present invention before installation in the mouth of a patient to improve various skeletal jaw conditions in people of various ages. The biased palatal expander device of the present invention 1 has a pair of expansion assemblies beginning with tubes 2, generally cylindrical and hollow, mutually parallel and spaced apart. Each tube has two opposite ends with one end having a base 3 and the other end 4 being open. Extending away from the base, the tube has a wall 2a having a thickness, visible at the open end 4.

From the open end 4, a rod 5 extends outwardly from the tube generally opposite the base. The rod has a cylindrical shape of lesser diameter than the tube and telescopes from within the tube 2 from the open end 4. The rod has a fixed end 6 generally opposite the tube and a free end, not shown, locating within the tube. The rod has sufficient length leaving a portion within the tube to prevent the rod from falling out of the tube during installation and usage. Each tube has a rod extending therefrom, mutually parallel and spaced apart. The centerline of each rod is collinear with the centerline of each tube.

Coaxial with each rod, a spring 7 surrounds the rod and extends from the open end 4 of the tube to the fixed end 6 of the rod. The spring has an inner diameter that exceeds the outer diameter of the rod, thus allowing the rod to move axially within the spring. The outer diameter of the spring is generally similar to the outer diameter of the tube thus allowing the spring to rest upon the thickness of the tube at the open end 4.

Inwardly from each base 3, a first bar 8 joins beneath the tubes 2. The bar is approximately one diameter inward from the bases. The bar is generally elongated and has two opposite ends. Each end has a shoulder 9 that tapers slightly to a neck 10. Upon the neck, an eyelet 11 attaches to the bar. The eyelet has a hollow, round shape and joins to the neck so that the diameter of the eyelet is collinear with the longitudinal axis of the bar. The diameter of the eyelet also is generally parallel to the longitudinal axis of the tube. The eyelets have a diameter generally greater than the width of the bar and a height similar to that of the width of the bar. And, inwardly from each fixed end 6, a second bar 12 joins beneath the rods 5. This bar is approximately one diameter inward from the fixed ends. This bar is generally elongated and has two opposite ends. Each end has a shoulder 9 that tapers slightly to a neck 10. Upon the neck, an eyelet 11 attaches to the bar. The eyelet has a hollow, round shape and joins to the neck so that the diameter of the eyelet is collinear with the longitudinal axis of the bar and generally parallel to the longitudinal axis of the tube. The eyelets have a diameter generally greater than the width of the bar and a height similar to that of the width of the bar. This bar 12 has two spacers 13 locating beneath the fixed ends 6 as later shown in FIG. 3. The spacers have a thickness similar to the thickness of the wall of the tube. The spacers provide that the four eyelets of the invention occupy the same plane for precise application of expansive force to the palate of a patient. As shown in FIG. 1, each tube and rod has a cooperating spring. The springs are generally located upon the same side of the invention for even and symmetric application of expansive forces. Alternatively, the springs can have locations upon opposite sides of the invention for an asymmetric application of force with slight rotation to meet the treatment plan for a patient.

Figure 2:
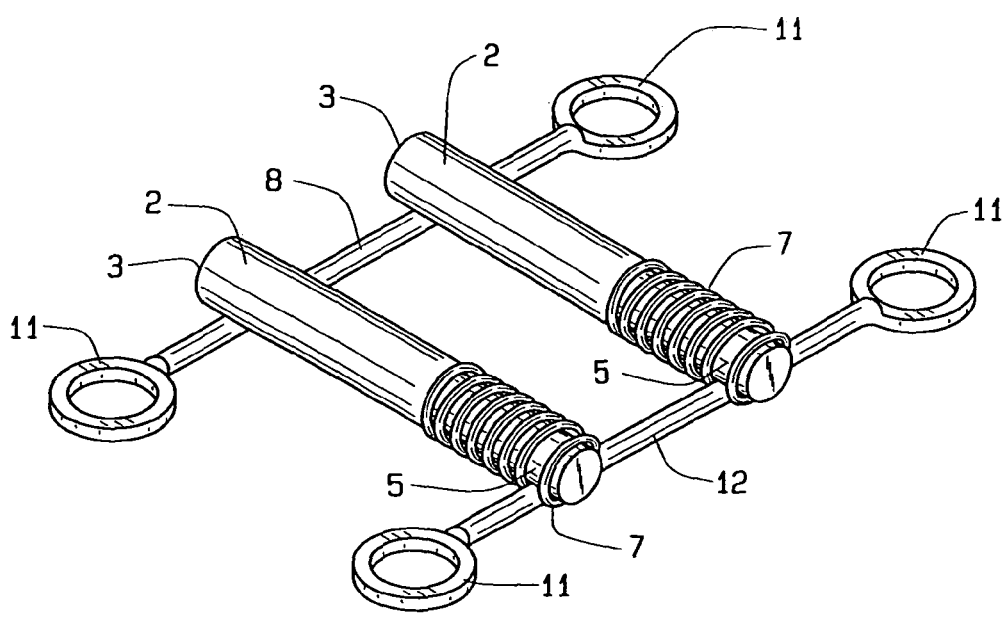
FIG. 2 describes an isometric view of the invention.

FIG. 2 shows an isometric view of the invention with two eyelets 11 in the foreground. As before, two mutually parallel and spaced apart rods 5 attach to a second bar 12 upon one of their ends, as at 6. The rods pass through cooperating springs 7 and enter tubes 2. The tubes have a hollow cylindrical shape with a base 3 opposite the entry point of the rods as at 4. The tubes attach to a bar 8 proximate the bases. Each bar has two opposite ends with an eyelet 11 upon each end. The eyelets have a hollow short cylindrical shape and attach to the bars at a point and the diameter of each eyelet is collinear with the longitudinal axis of the adjacent bar. The springs supply an expansive force generally outwardly from the tubes that urges the second bar 12 away from the bar 8.

Having described the components of the biased palatal expander, its operation will be briefly explained. Following molds and analysis of the patient's mouth, the orthodontist or oral surgeon determines where and in which direction to widen the palate of the patient. The device is secured in a closed position where the springs are compressed as the rods are temporarily held together, such as by looped wire. The patient is then sedated for preparation and installation of the invention. The orthodontist or oral surgeon then marks a line upon the palate of the patient indicating the direction of expansion. If needed, the oral surgeon performs an osteomy, breaking the palatal bone to allow its movement. The orthodontist then positions the device so that the eyelets 11 face towards the palate and the rods 5 and tubes 2 are centered upon the marked line. With the device positioned, the orthodontist or oral surgeon then drills pilot holes through the eyelets into the palatal bone. The orthodontist or oral surgeon then secures a screw through each eyelet into the pilot holes in the palatal bone. When the orthodontist or oral surgeon has completed installation of the device, the looped wire is removed and the springs expand the bars mutually outward. The bars transmit the lateral forces to the eyelets 11 and then through the mounting screws into the palate. Over time, the lateral forces widen the jaw as prescribed by the orthodontist.

Figure 3:
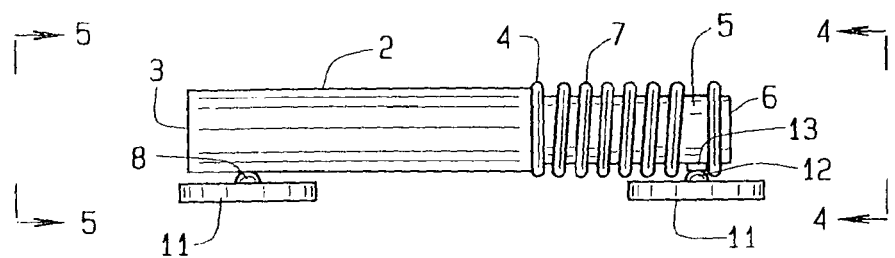
FIG. 3 illustrates a side view.

FIG. 3 shows an accommodation between the bars 8, 12 for level application of expansive force that minimizes the force directed axially into the screws. The tubes 2 have an outside diameter and an inside diameter. The inside diameter of the tubes admits the outside diameter of the rods. As the rods telescope from the tubes, as at 4, the rods have a lesser outside diameter than the inside and the outside diameters of the tubes. In usage, the fixed end 6 of a rod is slightly above the lowest point of a tube. Mounting the fixed ends 6 of the rods upon identical bars, as at 8, would provide one bar higher than the other. An offset in bar position would then provide a vertical force upon one bar leading to an imprecise application of expansive forces from the springs 7 through the eyelets. The present invention overcomes the offset between the rods and the tubes through use of spacers, as at 13. The spacers are located upon the second bar 12 generally beneath the fixed end 6 of the rods. The spacers have a thickness similar to the wall thickness of the tubes. The spacers are joined to the bar 12 and the rods 5, preferably by welding. The spaces then provide the second bar at the same elevation as the bar and that the four eyelets are in the same plane. Alternatively, the thickness of the second bar 12 exceeds that of the bar 8 by the thickness of the wall of a tube.

Figure 4:
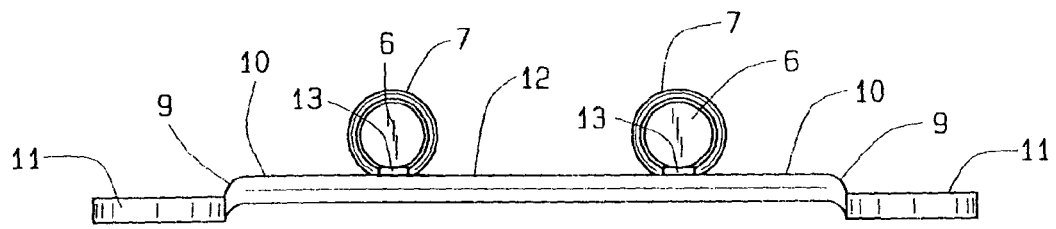
FIG. 4 shows an end view of the invention, the rods in the foreground.

FIG. 4 then provides an end view of the second bar 12 with the rods 5 attaching on their fixed ends 6 to the spacers 13. The springs 7 are shown with the rods locating coaxially within them. The rods have a generally symmetrical arrangement upon the bar and attach perpendicular to the bar. Outwardly from the spacers, the bar has a shoulder 10 proximate each end where the bar narrows slightly at the neck 9 to which an eyelet 11 joins. The eyelets upon this bar 12 generally occupy the same plane and the plane of the eyelets upon the other bar 8.

Figure 5:
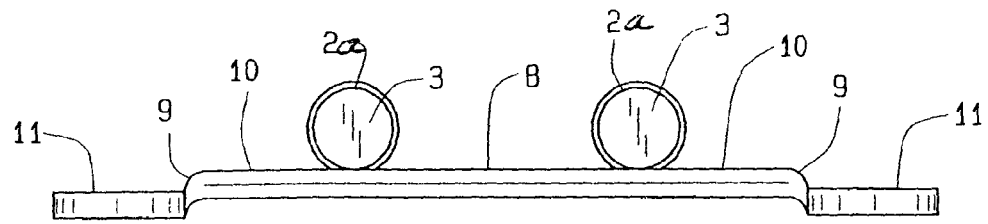
FIG. 5 shows an end view of the invention, the tubes in the foreground, opposite that of FIG. 4.

Then opposite FIG. 4, FIG. 5 shows another end view of the invention with the bases 3 of the tubes 2 attaching to the bar 8. The tubes attach perpendicular to the bar, generally symmetrically. As the thickness of the wall of the tubes establishes the position of the rods above the second bar 12, the tubes do not require a spacer upon this bar 8. Outwardly from the tubes, the bar 8 also has a shoulder 10 near each end that allows the bar to narrow slightly at the neck 9 to which an eyelet 11 joins. The eyelets upon this bar generally occupy the same plane and the plane of the eyelets upon the second bar 12. Having the eyelets upon the same plane allows for precise application of expansive forces from the springs outwardly upon the upper jaw without loss of force misdirected into the palatal bone.

In an alternate embodiment, the invention has a shell that receives the device upon a generally centered shelf. The flat shelf, a section of the shell, has a slightly narrower width than the device and more particularly less than the length of the bars including eyelets. The device has its eyelets locating outside from the shelf for proper positioning. The shelf connects two halves that fit the shell upon the upper molars of a patient and position the device upon the palate for installation.

The halves generally fit over at least three molars, in the mouth of a patient. The halves include a concave cross section to admit the teeth with a length proportional to at least three molars. Each half has depressions, shaped as individual teeth, for accurate positioning of the shell upon the teeth resulting in a precisely located device. The halves merged with the shelf towards a common end of the halves, generally towards the direction of the molars. Each end of a half extends away from the tooth depressions at the lowest point of the halfs cross section. The ends rise from the halves to a height for locating the shelf upon the palate.

Variations or modifications to the subject matter of this development may occur to those skilled in the art upon review of the invention as described herein. Such variations, if within the spirit of this development, are intended to be encompassed within the scope of the invention as explained. The description of the preferred embodiment and as shown in the drawings, are set forth for illustrative purposes only to show the principle and operations of this palatal distraction appliance that attaches directly to the palate of a patient and not the patient's teeth for expansion or contraction of the palate laterally or longitudinally.

I claim:

1. A device that expands the palate to alter the width or the length of the maxillary jaw of a person, said device securing to the palate and applying forces incrementally, said device further comprising:
   a pair of expansion assemblies, mutually parallel and spaced apart, each of said expansion assemblies having a base and an opposite fixed end;
   a first bar joining to said bases generally perpendicular to said expansion assemblies, said first bar having an elongated shape, a longitudinal axis, two opposite ends and an eyelet at each end wherein the plane of each eyelet locates away from the longitudinal axis, said eyelets having diameters parallel to the plane defined by said expansion assemblies;
   a second bar joining to said fixed ends generally perpendicular to said expansion assemblies and mutually parallel and spaced apart from said first bar, said second bar having an elongated shape, a longitudinal axis, two opposite ends and an eyelet at each end wherein the plane of each eyelet locates away from the longitudinal axis, said eyelets having diameters parallel to the plane defined by said expansion assemblies;
   said second bar being offset from said fixed ends wherein the eyelets of said first bar and said second bar occupy a common plane;
   said expansion assemblies including a tube, generally cylindrical with two opposite ends, said tube being closed upon one end defining said base and open upon the opposite end, a spring abutting the open end of said tube and extending coaxially away from said tube, and a rod, generally cylindrical with a free end and an opposite end defining said fixed end, said rod locating within said spring and entering the open end of said tube; and
   a spacer provided between the second bar and said rods to maintain the eyelets in a common plane.

2. The palate expanding device of claim 1 further comprising:
   at least four fasteners, said fasteners being placed through said eyelets and capable of securing into a the palatal bone thus securing said device to a person during usage.

* * * * *